United States Patent
Griffin et al.

(10) Patent No.: US 12,233,264 B2
(45) Date of Patent: Feb. 25, 2025

(54) HEARING DEVICE AND METHOD OF USING SAME

(71) Applicant: STARKEY LABORATORIES, INC., Eden Prairie, MN (US)

(72) Inventors: Kendra Griffin, Fort Lauderdale, FL (US); Justin R. Burwinkel, Eden Prairie, MN (US); Michael Karl Sacha, Chanhassen, MN (US)

(73) Assignee: STARKEY LABORATORIES, INC., Eden Prairie, MN (US)

( * ) Notice: Subject to any disclaimer, the term of this patent is extended or adjusted under 35 U.S.C. 154(b) by 281 days.

(21) Appl. No.: 18/076,457

(22) Filed: Dec. 7, 2022

(65) Prior Publication Data
US 2023/0173272 A1    Jun. 8, 2023

Related U.S. Application Data

(60) Provisional application No. 63/286,780, filed on Dec. 7, 2021.

(51) Int. Cl.
*H04R 25/00* (2006.01)
*A61B 5/0205* (2006.01)
*A61N 1/36* (2006.01)

(52) U.S. Cl.
CPC ........ *A61N 1/36038* (2017.08); *A61B 5/0205* (2013.01); *H04R 25/00* (2013.01)

(58) Field of Classification Search
CPC ....... A61B 5/0205; A61B 5/6817; A61B 5/05; A61B 5/11; A61B 5/126; A61B 5/16; A61B 5/24; A61N 1/36038; H04R 25/00; H04R 25/305
See application file for complete search history.

(56) References Cited

U.S. PATENT DOCUMENTS

| 8,270,623 B2 | 9/2012 | Hamilton et al. |
| 8,358,787 B2 | 1/2013 | Lee et al. |
| 8,824,712 B2 * | 9/2014 | Sacha ............ H04R 25/50 381/324 |
| 8,942,399 B2 | 1/2015 | Salameh |

(Continued)

FOREIGN PATENT DOCUMENTS

EP    2814263    11/2017

OTHER PUBLICATIONS

U.S. Provisional Application for Method and Apparatus for Behind-The-Ear Hearing Aid With Capacitive Sensor, Inventor: Michael Karl Sacha, Filed Oct. 19, 2019 (25 pages).

*Primary Examiner* — Brian Ensey
(74) *Attorney, Agent, or Firm* — Mueting Raasch Group

(57) ABSTRACT

Various embodiments of a hearing device and a method of using such device are disclosed. The hearing device includes a housing having an inner surface and an outer surface, electronic components disposed within the housing, and a port disposed in the housing and extending between a first end at the outer surface of the housing and a second end disposed within the housing, where the port is acoustically connected to at least one of a speaker or a microphone of the electronic components. The hearing components also include a controller that is electrically connected to a sensor and that is adapted to detect a change in capacitance of the sensor, where the change in capacitance is associated with debris at least partially occluding the port.

20 Claims, 10 Drawing Sheets

(56) References Cited

U.S. PATENT DOCUMENTS

| | | | |
|---|---|---|---|
| 9,351,068 B2 | 5/2016 | Slupeiks et al. | |
| 9,860,659 B2 | 1/2018 | Won et al. | |
| 9,924,288 B2 | 3/2018 | Cagdaser et al. | |
| 10,209,123 B2 * | 2/2019 | Vitt | G01H 15/00 |
| 10,715,940 B2 | 7/2020 | Keady et al. | |
| 10,768,067 B2 | 9/2020 | Arndt et al. | |
| 10,863,293 B2 | 12/2020 | Yan et al. | |
| 2014/0294182 A1 | 10/2014 | Axelsson et al. | |
| 2015/0022014 A1 | 1/2015 | Tanabe | |
| 2017/0350925 A1 | 12/2017 | Krogsgaard et al. | |
| 2020/0314526 A1 | 10/2020 | Lee et al. | |

* cited by examiner

HEARING DEVICE AND METHOD OF USING SAME

This application claims the benefit of U.S. Provisional Application No. 63/286,780, filed Dec. 7, 2021, the disclosure of which is incorporated by reference herein in its entirety.

BACKGROUND

Ingress of debris such as earwax into a port of a hearing device can inhibit the functionality of such device. Ingress of such debris can cause low-throughput distortion, reduction in high-frequency gains (approximately 10-15 dB in mid to high frequencies), decreased hearing or increased tinnitus due to device malfunction, or even render the device unusable. Similarly, debris can also affect sensors, interfering with contact with or visibility to the skin, thereby potentially yielding false or absent readings. Debris can also affect the seal of the hearing device with an ear of a user and cause improper fit. Debris can also cause undesirable sound reflections within the ear canal, which in turn can create unwanted acoustic feedback to the device's microphone. These issues can cause unnecessary frustration for users and reduce the time that the devices are usable especially if these devices require servicing by a technician.

SUMMARY

In general, the present disclosure provides various embodiments of a hearing device and a method of using such hearing device. The hearing device can include a housing and one or more ports that are disposed in the housing. The device can also include a sensor disposed adjacent to or at least partially within at least one of the ports. The sensor can be electrically connected to a controller disposed within the housing. Further, the sensor can be utilized to detect whether a port is at least partially occluded by debris.

In one aspect, the present disclosure provides a hearing device that includes a housing having an inner surface and an outer surface; electronic components disposed within the housing and including a speaker, a microphone, and a controller electrically connected to the speaker and the microphone; and a port disposed in the housing and extending between a first end at the outer surface of the housing and a second end disposed within the housing, where the port is acoustically connected to at least one of the speaker or the microphone. The hearing device further includes a sensor having a first electrode and a second electrode each electrically connected to the controller, where the first electrode is disposed at least partially within the first end of the port, and further where the second electrode is disposed on the outer surface of the housing and spaced apart from the first electrode. The controller is adapted to detect a change in capacitance of the sensor, where the change in capacitance is associated with debris at least partially occluding the port.

In another aspect, the present disclosure provides a hearing device that includes a housing having an acoustic port disposed through the housing, and hearing components disposed within the housing and including a speaker and a controller electrically connected to the speaker, where the speaker is acoustically connected to the acoustic port, and where the speaker includes first and second diaphragms. The controller is adapted to direct an acoustic signal to the first diaphragm such that the first diaphragm converts the acoustic signal to a reference sound wave that is transmitted into an ear canal through the acoustic port; detect a second sound wave utilizing the second diaphragm, where the second sound wave includes at least a portion of the reference sound wave that is reflected by an eardrum within the ear canal and directed into the acoustic port; and compare a sound pressure level of the reference sound wave to a sound pressure level of the second sound wave. The controller is further adapted to determine whether the acoustic port is at least partially occluded by debris based upon the comparison of the sound pressure level of the reference sound wave to the sound pressure level of the second sound wave.

In another aspect, the present disclosure provides a hearing device that includes a housing having a microphone port disposed through the housing, and hearing components disposed within the housing and including a microphone and a controller electrically connected to the microphone, where the microphone is acoustically connected to the microphone port and includes a diaphragm. The controller is adapted to direct a first electrical pulse to the microphone diaphragm; determine a reference decay rate of a mechanical resonance signal of the microphone diaphragm in response to the first electrical pulse when the microphone port is unobstructed; and direct a second electrical pulse to the microphone diaphragm. The controller is further adapted to determine a second decay rate of a second mechanical resonance signal of the microphone diaphragm in response to the second electrical pulse; compare the reference decay rate to the second decay rate; and determine whether the microphone port is at least partially occluded by debris if the second decay rate is greater than the reference decay rate.

In another aspect, the present disclosure provides a method that includes detecting a sound pressure level of acoustic energy emitted by a hearing device; comparing the detected sound pressure level to a reference sound pressure level of acoustic energy emitted by the hearing device; and, if the detected sound pressure level is less than the reference sound pressure level, then comparing a power level of a power source of the hearing device to an operating threshold. The method further includes, if the power level is above the operating threshold, then determining whether at least one of an acoustic port or a microphone port is at least partially occluded by debris; and notifying a user or a technician if at least one of the acoustic port or the microphone port is at least partially occluded.

All headings provided herein are for the convenience of the reader and should not be used to limit the meaning of any text that follows the heading, unless so specified.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements.

In this application, terms such as "a," "an," and "the" are not intended to refer to only a singular entity but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

These and other aspects of the present disclosure will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWINGS

Throughout the specification, reference is made to the appended drawings, where like reference numerals designate like elements, and wherein.

DETAILED DESCRIPTION

Figure 1:
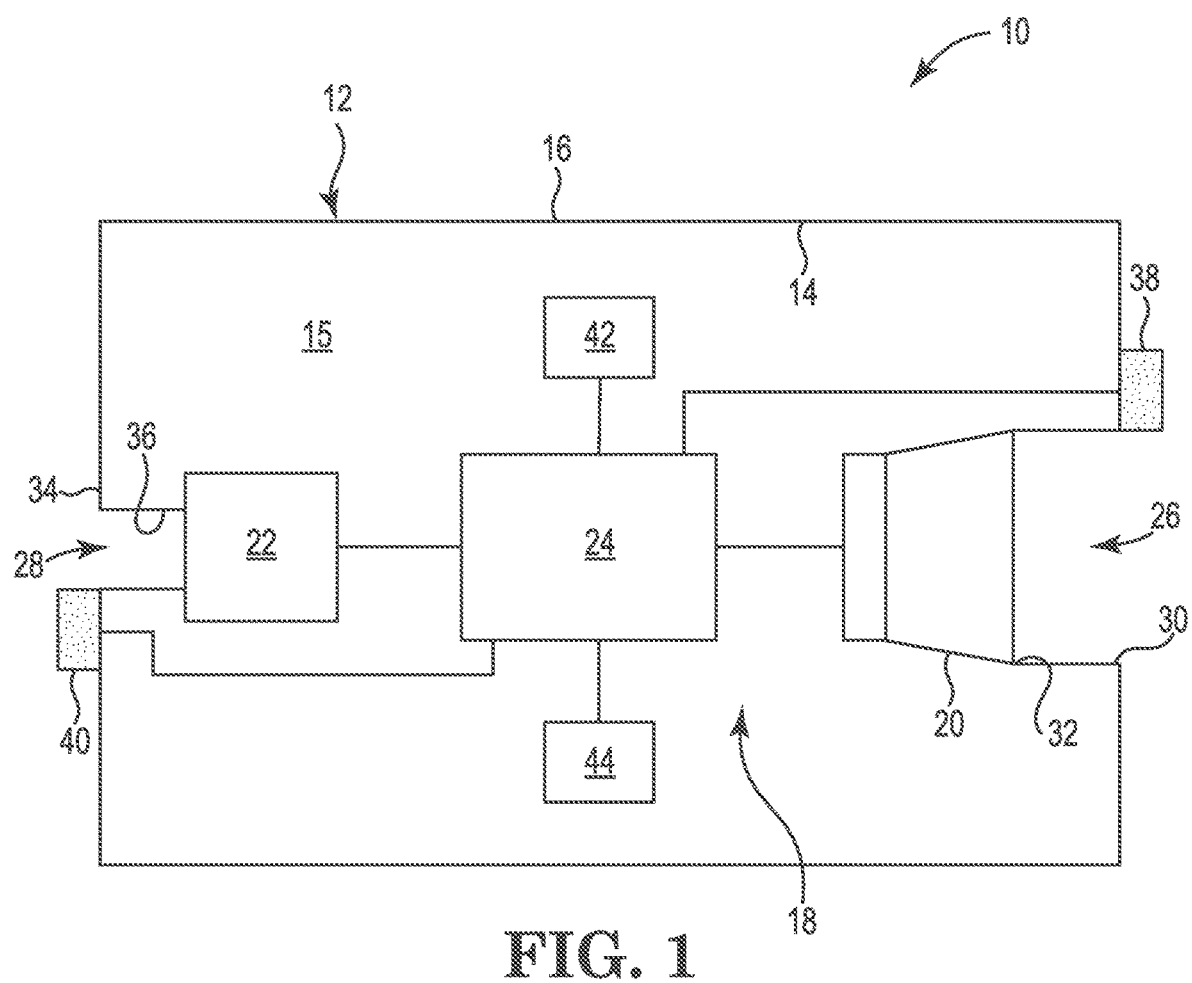
FIG. 1 is a schematic plan view of one embodiment of a hearing device.

In general, the present disclosure provides various embodiments of a hearing device and a method of using such hearing device. The hearing device can include a housing and one or more ports that are disposed in the housing. The device can also include a sensor disposed adjacent to or at least partially within at least one of the ports. The sensor can be electrically connected to a controller disposed within the housing. Further, the sensor can be utilized to detect whether a port is at least partially occluded by debris.

Diminished performance of a hearing device caused by ingress of debris such as earwax can frustrate a user of such device. This frustration can lead a user to request immediate attention from hearing care professionals. Due to the urgency of the potential issues cause by debris ingress (e.g., diminished sound quality), a hearing device provider may be required to provide unreimbursed appointments to the user to deliver what are oftentimes simple solutions. Wax filters or traps disposed over or within ports of the hearing device can reduce the negative effects of debris ingress. Users may, however, fail to change these wax filters. Further, wax filters can be difficult to change because of visual or dexterity limitations of the user.

One or more embodiments of a hearing device and a method utilized by the hearing device described herein can allow users to more efficiently resolve these issues on their own, thereby reducing the level of frustration with the devices. In one or more embodiments, a hearing device can include a sensor disposed adjacent to or at least partially within a port of the device. Such sensor can include any suitable sensor such as a capacitive sensor that is adapted to detect a change in capacitance between two electrodes of the sensor. Such capacitive sensing of debris that at least partially occludes a port can be performed on a continuous basis, i.e., while the hearing device is in use. Further, debris accumulation remote from the port, e.g., on a housing of the device, can be performed using the sensor when the hearing device is not in use. One or more embodiments of the present disclosure may also eliminate the need for wax filters or traps.

Embodiments of the disclosure are defined in the claims; however, herein there is provided a non-exhaustive listing of non-limiting examples. Any one or more of the features of these examples may be combined with any one or more features of another example, embodiment, or aspect described herein.

Example Ex1. A hearing device that includes a housing having an inner surface and an outer surface; electronic components disposed within the housing and including a speaker, a microphone, and a controller electrically connected to the speaker and the microphone; and a port disposed in the housing and extending between a first end at the outer surface of the housing and a second end disposed within the housing, where the port is acoustically connected to at least one of the speaker or the microphone. The hearing device further includes a sensor having a first electrode and a second electrode each electrically connected to the controller, where the first electrode is disposed at least partially within the first end of the port, and further where the second electrode is disposed on the outer surface of the housing and spaced apart from the first electrode. The controller is adapted to detect a change in capacitance of the sensor, where the change in capacitance is associated with debris at least partially occluding the port.

Example Ex2. The hearing device of Ex1, where the port includes an acoustic port, and where the speaker is acoustically connected to the acoustic port.

Example Ex3. The hearing device of Ex1, where the port includes a microphone port, where the microphone is acoustically connected to the microphone port.

Example Ex4. The hearing device of one or more of Ex1 to Ex3, where the debris includes wax.

Example Ex5. The hearing device of one or more of Ex1 to Ex4, where the hearing device includes a hearing assistance device.

Example Ex6. The hearing device of Ex5, where the hearing assistance device includes a receiver-in-the-ear hearing device.

Example Ex7. The hearing device of one or more of Ex1 to Ex6, where at least one of the first electrode or the second electrode includes a ring electrode.

Example Ex8. The hearing device of one or more of Ex1 to Ex7, where the second electrode encircles the first electrode and the first end of the port.

Example Ex9. The hearing device of one or more of Ex1 to Ex8, where the first electrode is disposed entirely within the port.

Example Ex10. The hearing device of Ex9, where the controller is further adapted to notify a user or technician that the port is at least partially occluded if a change of capacitance is detected.

Example Ex11. A hearing device that includes a housing having an acoustic port disposed through the housing, and hearing components disposed within the housing and including a speaker and a controller electrically connected to the speaker, where the speaker is acoustically connected to the acoustic port, and where the speaker includes first and second diaphragms. The controller is adapted to direct an acoustic signal to the first diaphragm such that the first diaphragm converts the acoustic signal to a reference sound wave that is transmitted into an ear canal through the acoustic port; detect a second sound wave utilizing the second diaphragm, where the second sound wave includes at least a portion of the reference sound wave that is reflected by an eardrum within the ear canal and directed into the acoustic port; and compare a sound pressure level of the reference sound wave to a sound pressure level of the second sound wave. The controller is further adapted to determine whether the acoustic port is at least partially occluded by debris based upon the comparison of the sound pressure level of the reference sound wave to the sound pressure level of the second sound wave.

Example Ex12. The hearing device of Ex11, where the debris includes wax.

Example Ex13. The hearing device of one or more of Ex11 to Ex12, where the hearing device includes a hearing assistance device.

Example Ex14. The hearing device of Ex13, where the hearing assistance device includes a receiver-in-the-ear hearing device.

Example Ex15. The hearing device of one or more of Ex11 to Ex14, where the controller is further adapted to notify a user or technician that the acoustic port is at least partially occluded based upon the comparison of the sound pressure level of the reference sound wave to the sound pressure level of the second sound wave.

Example Ex16. A hearing device that includes a housing having a microphone port disposed through the housing, and hearing components disposed within the housing and including a microphone and a controller electrically connected to the microphone, where the microphone is acoustically connected to the microphone port and includes a diaphragm. The controller is adapted to direct a first electrical pulse to the microphone diaphragm; determine a reference decay rate of a mechanical resonance signal of the microphone diaphragm in response to the first electrical pulse when the microphone port is unobstructed; and direct a second electrical pulse to the microphone diaphragm. The controller is further adapted to determine a second decay rate of a second mechanical resonance signal of the microphone diaphragm in response to the second electrical pulse; compare the reference decay rate to the second decay rate; and determine whether the microphone port is at least partially occluded by debris if the second decay rate is greater than the reference decay rate.

Example Ex17. The hearing device of Ex16, where the debris includes wax.

Example Ex18. The hearing device of one or more of Ex16 to Ex17, where the hearing device includes a receiver-in-the-ear hearing device.

Example Ex19. The hearing device of one or more of Ex16 to Ex18, where the microphone includes a microelectromechanical microphone.

Example Ex20. The hearing device of one or more of Ex16 to Ex19, where the controller is further adapted to notify a user or technician that the microphone port is at least partially occluded if the second decay rate is greater than the reference decay rate.

Example Ex21. The hearing device of one or more of Ex16 to Ex20, where the hearing components further include a speaker acoustically connected to an acoustic port that is disposed through the housing.

Example Ex22. The hearing device of Ex21, where the controller is further adapted to direct an acoustic signal to the speaker such that the speaker converts the acoustic signal to a reference sound wave that is transmitted into an ear canal through the acoustic port; detect a second sound wave utilizing the second diaphragm, where the second sound wave includes at least a portion of the reference sound wave that is reflected by an eardrum within the ear canal and directed into the acoustic port; and compare a sound pressure level of the reference sound wave to a sound pressure level of the second sound wave. The controller is further adapted to determine whether the acoustic port is at least partially occluded based upon the comparison of the sound pressure level of the reference sound wave to the sound pressure level of the second sound wave.

Example Ex23. The hearing device of Ex22, where the controller is further adapted to notify a user or technician that the acoustic port is at least partially occluded based upon the comparison of the sound pressure level of the reference sound wave to the sound pressure level of the second sound wave.

Example Ex24. The hearing device of one or more of Ex16 to Ex23, where the second electrical pulse includes a bias voltage pulse.

Example Ex25. A method that includes detecting a sound pressure level of acoustic energy emitted by a hearing device; comparing the detected sound pressure level to a reference sound pressure level of acoustic energy emitted by the hearing device; and, if the detected sound pressure level is less than the reference sound pressure level, then comparing a power level of a power source of the hearing device to an operating threshold. The method further includes, if the power level is above the operating threshold, then determining whether at least one of an acoustic port or a microphone port is at least partially occluded by debris; and notifying a user or a technician if at least one of the acoustic port or the microphone port is at least partially occluded.

Example Ex26. The method of Ex25, further including removing the debris from at least one of the acoustic port or microphone port.

Example Ex27. The method of one or more of Ex25 to Ex26, where determining whether at least one of the acoustic port or microphone port is at least partially occluded by debris includes measuring a reference capacitance between a first electrode disposed at least partially within the acoustic port or the microphone port and a second electrode disposed on a housing of the hearing device when each of the acoustic port and microphone port is unobstructed; measuring a second capacitance between the first electrode and the second electrode; and determining that the acoustic port or microphone port is at least partially occluded if the second capacitance is greater than the reference capacitance.

Example Ex28. The method of one or more of Ex25 to Ex26, where determining whether at least one of the acoustic port or microphone port is at least partially occluded by debris includes directing a first electrical pulse to a diaphragm of a microphone disposed in a housing of the hearing device, where the microphone is acoustically connected to the microphone port; determining a reference decay rate of a mechanical resonance signal of the microphone diaphragm in response to the first electrical pulse when the microphone port is unobstructed; and directing a second electrical pulse to the microphone diaphragm. The method further includes determining a second decay rate of a second mechanical resonance signal of the microphone diaphragm in response to the second electrical pulse; comparing the reference decay rate to the second decay rate; and determining that the microphone port is at least partially occluded by debris if the second decay rate is greater than the reference decay rate.

Example Ex29. The method of Ex28, further including determining that the acoustic port is at least partially occluded by debris if the second decay rate is substantially equal to the reference decay rate.

Example Ex30. The method of one or more of Ex25 to Ex26, where determining whether at least one of the acoustic port or microphone port is at least partially occluded by debris includes directing an acoustic signal to a first diaphragm of a speaker disposed within a housing of the hearing device and acoustically connected to the acoustic port such that the first diaphragm converts the acoustic signal to a reference sound wave that is transmitted into an ear canal through the acoustic port; detecting a second sound wave utilizing a second diaphragm of the speaker, where the second sound wave includes at least a portion of the reference sound wave that is reflected by an eardrum within the ear canal and directed into the acoustic port; comparing a sound pressure level of the reference sound wave to a sound pressure level of the second sound wave; and determining whether the acoustic port is at least partially occluded based upon the comparison of the sound pressure level of the reference sound wave to the sound pressure level of the second sound wave.

FIG. 1 is a schematic plan view of one embodiment of a hearing device 10. The device 10 includes a housing 12 that has an inner surface 14 and an outer surface 16. Further, the device 10 includes one or more electronic components 18 disposed within the housing 12, including at least one of a speaker 20, a microphone 22, and a controller 24 electrically connected to the speaker and the microphone. Disposed in the housing 12 are one or more ports, including an acoustic port 26 and a microphone port 28. The acoustic port 26 extends between a first end 30 at the outer surface 16 of the housing 12 and a second end 32 disposed within the housing. Similarly, the microphone port 28 extends between a first end 34 at the outer surface 16 of the housing 12 and a second end 36 disposed within the housing. The acoustic port 26 is acoustically connected to the speaker 20, and the microphone port 28 is acoustically connected to the microphone 22. As used herein, the term "acoustically connected" means that a component is disposed in relation to another component such that acoustic energy can be transmitted between the two components.

The device 10 further includes one or more sensors. For example, as shown in FIG. 1, the device 10 includes a first sensor 38 disposed adjacent to the acoustic port 26. As used herein, the term "adjacent to the acoustic port" means that an element or component is disposed closer to the acoustic port 26 than to the microphone port 28. The device 10 also includes a second sensor 40 disposed adjacent to the microphone port 28. As used herein, the term "adjacent to the microphone port" means that an element or component is disposed closer to the microphone port 28 than to the acoustic port 26. Although depicted as including two sensors 38, 40, the device 10 can include any suitable number of sensors disposed in any suitable location, e.g., 1, 2, 3, 4, 5, or more sensors. In one or more embodiments, the controller 24 is adapted to detect whether debris such as earwax is at least partially occluding at least one of the acoustic port 26 or microphone port 28 utilizing one or more of the sensors 38, 40 as is further described herein.

The hearing device 10 can include any suitable device that can provide acoustic energy to a user using any suitable technique or techniques, e.g., by directing sound into an ear or ears of the user, bone conduction, implants, etc. In one or more embodiments, the hearing device 10 can include over-the-ear or in-ear headphones, an earpiece, etc. Further, in one or more embodiments, the hearing device 10 can include a hearing assistance device such as behind-the-ear (BTE), in-the-ear (ITE), in-the-canal (ITC), or completely-in-the-canal (CIC) type hearing devices. It is understood that behind-the-ear type hearing devices can reside substantially behind the ear or over the ear. Such devices can include receivers associated with an electronics portion of the behind-the-ear device, or receivers disposed in the ear canal of the user. Such devices are also known as receiver-in-the-canal (RIC) or receiver-in-the-ear (RITE) hearing devices. In one or more embodiments, the hearing device 10 can include an implantable hearing device, e.g., cochlear implant, brainstem implant, auditory nerve implant, or a bone-conduction or otherwise osseointegrated hearing device.

The various embodiments described herein can be utilized with any suitable number of hearing devices 10. For example, the user can wear two or more hearing devices simultaneously. In one or more embodiments, a user can wear a left hearing device that is adapted to be acoustically connected to the user's left ear and a right hearing device that is adapted to be acoustically connected to the user's right ear. In one or more embodiments, the left hearing device can electromagnetically communicate with the right hearing device using any suitable technique or techniques. The hearing device 10 can be adapted to be disposed at least partially within an ear canal of an ear of the user, behind the ear of the user, or at least partially disposed in the ear of the user.

The housing 12 of the hearing device 10 can take any suitable shape or shapes and have any suitable dimensions depending upon where the hearing device is intended to be disposed. For example, for BTE hearing devices, the housing 12 is shaped such that it can be disposed behind the ear of the user between the ear and a skull of the user. Further, for example, for RIC hearing devices, the housing 12 is shaped such that at least a portion of the housing can be disposed within an ear canal (not shown) of the user. Further, the housing 12 can include any suitable material or materials, e.g., at least one of a metallic, polymeric, or inorganic material.

Disposed within the housing 12 of the hearing device 10 are the electronic components 18. The electronic components 18 can include any suitable device or devices, e.g., integrated circuits, power sources, microphones, speakers (i.e., receivers), etc. For example, in one or more embodiments, the components 18 can include the speaker 20, the microphone 22, the controller 24, a power source 42, and an antenna 44. The speaker 20, microphone 22, power source 42, and antenna 44 can be electrically connected to the controller 24 using any suitable technique or techniques.

The speaker 20 of the hearing device 10 can include any suitable speaker or speakers. Although one speaker 20 is depicted, the components 18 can include any suitable number of speakers. In one or more embodiments, the speaker 20 can include a dual-motor speaker as is further described herein in reference to FIG. 6. The speaker 20 can be disposed in any suitable location within the housing 12. In one or more embodiments, the speaker 20 is acoustically connected to the speaker port 26 and is adapted to direct acoustic energy through the speaker port to the user.

The electronic components 18 can also include the microphone 22. Although one microphone 22 is depicted, the components 18 can include any suitable number of microphones. Further, the microphone 22 can be disposed in any suitable location within the housing 12. For example, in one or more embodiments, the microphone 22 is acoustically connected to the microphone port 28 and is adapted to receive audio information from the user's environment. Any suitable microphone 22 can be utilized. In one or more embodiments, the microphone 22 can include a microelectromechanical (MEMS) microphone as is further described herein in reference to FIGS. 7-8.

Further, the electronic components 18 can include the controller 24. Any suitable controller 24 can be utilized with the hearing device 10. For example, in embodiments where the hearing device 10 is utilized as a hearing assistance device, the controller 24 can be adapted to employ programmable gains to adjust the hearing device output to the user's hearing impairment. The controller 24 can be a digital signal processor (DSP), microprocessor, microcontroller, other digital logic, or combinations thereof. The processing can be done by a single processor or can be distributed over different devices. The processing of signals referenced in this disclosure can be performed using the controller 24 or over different devices.

Such processing may be done in the digital domain, the analog domain, or combinations thereof. Processing may be done using subband processing techniques. Processing may be done using frequency domain or time domain approaches. Some processing may involve both frequency and time domain aspects. For brevity, in some examples, drawings may omit certain blocks that perform frequency synthesis, frequency analysis, analog-to-digital conversion, digital-to-analog conversion, amplification, buffering, and certain types of filtering and processing. In one or more embodiments, the controller 24 or other processing devices execute instructions to perform signal processing tasks. Such embodiments can include analog components in communication with the controller 24 to perform signal processing tasks, such as sound reception by the microphone 22, or playing of sound using the speaker 20.

The power source 42 of the electronic components 18 can include any suitable power source, e.g., at least one of a battery, inductively-charged capacitor, etc. Although depicted as including one power source 42, the components 18 can include any suitable number of power sources disposed in any suitable location within the housing 12. Further, the power source 42 can be electrically connected to the controller 24 and at least one of the speaker 20, microphone 22, or antenna 44, or any other components disposed on or within the housing 12. For example, the power source 42 can be directly electrically connected to at least one of the first sensor 38 or the second sensor 40.

The electronic components 18 can also include the antenna 44. Any suitable antenna or combination of antennas can be utilized. In one or more embodiments, the antenna 44 can include one or more antennas having any suitable configuration. Further, for example, antenna configurations can vary and can be included within the housing 12 or be external to the housing. The antenna 44 can be compatible with any suitable protocol or combination of protocols. In one or more embodiments, the components 18 can also include a transmitter that transmits electromagnetic signals and a radio-frequency receiver that receives electromagnetic signals using any suitable protocol or combination of protocols.

For example, in one or more embodiments, the hearing device 10 can be connected to one or more external devices using, e.g., Bluetooth, Wi-Fi, magnetic induction, etc. In one or more embodiments, the hearing device 10 can be wirelessly connected to the Internet using any suitable technique or techniques. Such connection can enable the hearing device 10 to access any suitable databases, including medical records databases, cloud computing databases, location services, etc. In one or more embodiments, the hearing device 10 can be wirelessly connected utilizing the Internet of Things (IoT) such that the hearing device can communicate with, e.g., hazard beacons, one or more cameras disposed in proximity to the user, motion sensors, room lights, etc.

In embodiments where the hearing device 10 includes a second hearing device disposed on an opposite side of the user's head, the antenna 44 can be utilized to communicate with an antenna of the second hearing device. In one or more embodiments, a low-power link across the user's head can be utilized to transmit electromagnetic signals between the first and second hearing devices.

As mentioned herein, the hearing device 10 includes the acoustic port 26 and the microphone port 28. Although depicted as including the acoustic port 26 and the microphone port 28, the hearing device 10 can include any suitable number and type of ports that extend between the outer surface 16 of the housing 12 and an interior space 15 of the hearing device.

The acoustic port 26, which extends between its first end 30 and its second end 32. The acoustic port 26 can take any suitable shape or shapes and have any suitable dimensions. Further, the acoustic port 26 can be disposed in any suitable portion or portions of the housing 12 of the hearing device 10. While depicted as being a unitary acoustic port 26, in one or more embodiments, the speaker port can include two or more channels that extend between the outer surface 16 of the housing 12 and the speaker 20 such that acoustic energy provided by the speaker can be directed through the acoustic port and beyond the housing 12 of the hearing device 10.

The acoustic port 26 can be acoustically connected to the speaker 20 using any suitable technique or techniques. In one or more embodiments, at least a portion of the speaker 20 can be disposed within the acoustic port 26 such that acoustic energy produced by the speaker can be directed through the acoustic port.

Further, the microphone port 28, which is acoustically connected to the microphone 22, can take any suitable shape or shapes and have any suitable dimensions. The microphone port 28 extends between its first end 34 at the outer surface 16 of the housing 12 and its second end 36, which is disposed within the housing. The microphone port 28 is adapted to direct the acoustic energy that is incident upon the port to the microphone 22, where such acoustic energy can be converted to one or more electrical signals that are then directed to the controller 24. Although depicted as including a single port, the microphone port 28 can include two or more ports that are adapted to direct incident acoustic energy to the microphone 22.

The microphone port 28 can be acoustically connected to the microphone 22 using any suitable technique or techniques. In one or more embodiments, one or more portions of the microphone 22 can be disposed within the microphone port 28 such that acoustic energy incident upon the microphone port can be directed to the microphone.

Electrically connected to the controller 24 are sensors 38, 40. Although depicted as including two sensors 38, 40, the hearing device 10 can include any suitable number of sensors, e.g., 1, 2, 3, 4, 5, or more sensors. The first sensor 38 is adapted to be utilized by the controller 24 to detect whether the acoustic port 26 is at least partially occluded by debris. Further, the second sensor 40 is adapted to be utilized by the controller 24 to detect whether the microphone port 28 is at least partially occluded by debris. The sensors 38, 40 can each include any suitable sensor or sensors, e.g., a capacitive sensor. In one or more embodiments, one efficient implementation for capacitive sensing is to use a GPIO pin(s) from processor 24 (FIG. 1). Otherwise, any general purpose microprocessor chip can be configured to yield capacitive sensing. Some manufacturers incorporate specific hardware within some processors that enhance capacitive sensing. These processors are not necessary for this application but can provide greater dynamic sensing range and sensitivity. In one or more embodiments, the controller 24 can be adapted to detect a change in capacitance using at least one of the sensors 38, 40.

In one or more embodiments, each of the sensors 38, 40 can include a sensor or sensors that can be utilized to detect one or more characteristics of the user, e.g., at least one of a physiological characteristic (e.g., pulse) or a contextual characteristic (e.g., ambient temperature) of the user. For example, at least one of the sensors 38, 40 can include a sensor that can detect one or more physiological characteristics of the user such as at least one of an accelerometer, barometer, gyroscope, heart rate sensor, blood pressure sensor, magnetometer, eye sensor, EEG sensor, blood sugar sensor, light sensor, sweat sensor, pupillometry sensor, cerumen sensor, cortisol sensor, body temperature sensor, humidity sensor, air quality sensor, or combinations thereof. Further, for example, at least one of sensors 38, 40 can include a sensor that can detect one or more contextual characteristics, such as at least one of an ambient temperature sensor, barometer, microphone, GPS sensor, moisture/humidity sensor, image sensor (i.e., a camera), or combinations thereof. The first sensor 38 can include the same sensor as the second sensor 40. In one or more embodiments, the first sensor 38 can include a sensor that is different from that of the second sensor 40. The sensors 38, 40 can be electrically connected to the controller 24 using any suitable technique or techniques.

Figure 2:
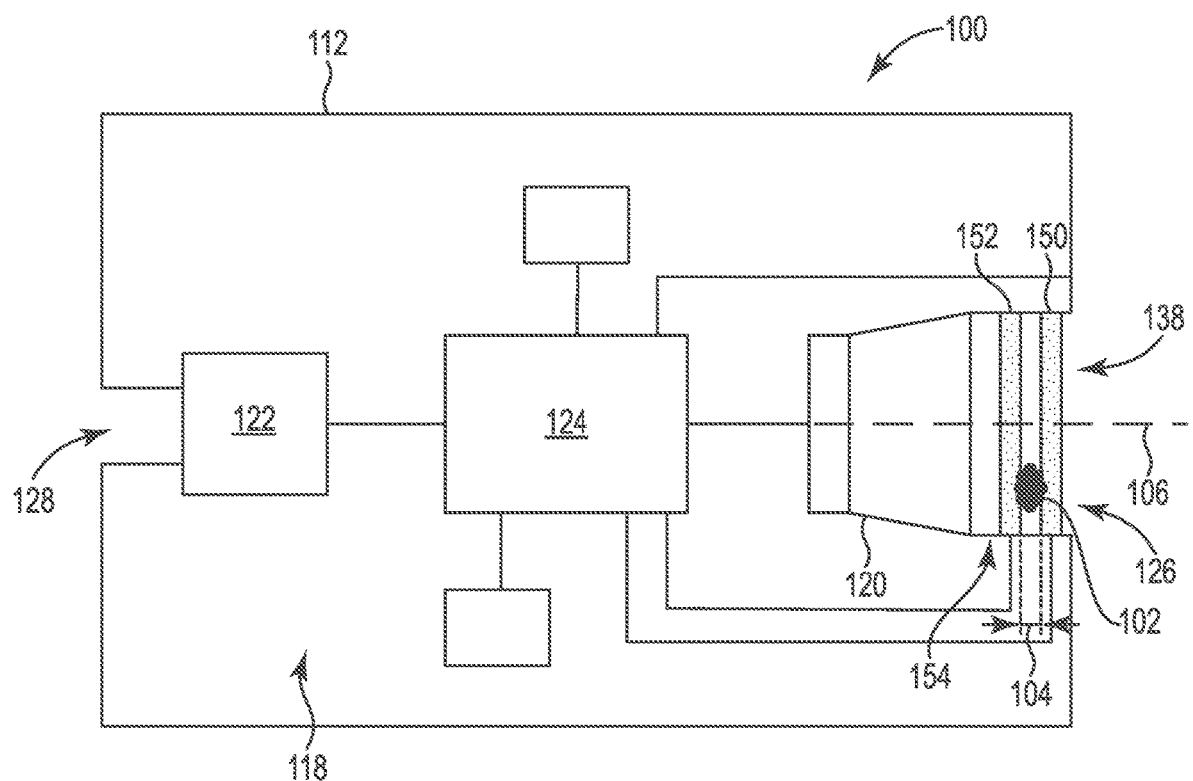
FIG. 2 is a schematic plan view of another embodiment of a hearing device.

Further, the sensors 38, 40 can be disposed in any suitable location relative to ports 26, 28 respectively and have any suitable configuration. For example, FIG. 2 is a schematic plan view of another embodiment of a hearing device 100. All of the design considerations and possibilities described herein regarding the hearing device 10 of FIG. 1 apply equally to the hearing device 100 of FIG. 2. The hearing device 100 includes a housing 112, electronic components 118 disposed within the housing, an acoustic port 126 disposed in the housing, and a sensor 138 disposed within the acoustic port. Although depicted as being disposed within the acoustic port 126, the sensor 138 can be disposed at least partially within a microphone port 128 of the hearing device 100. The electronic components 118 include a speaker 120 acoustically connected to the acoustic port 126, a microphone 122, and a controller 124. The controller 124 is electrically connected to the speaker 120 and the microphone 122.

The sensor 138 includes a first electrode 150 and a second electrode 152 spaced apart from the first electrode. Each of the first and second electrodes 150, 152 is electrically connected to the controller 124. As illustrated in FIG. 2, the first and second electrodes 150, 152 are disposed within the acoustic port 126. In one or more embodiments, at least one of the first and second electrodes 150, 152 can be disposed outside of the acoustic port 126 or partially within the acoustic port as is further described herein. Together, the first and second electrodes 150, 152 can form a capacitor 154 that can be utilized by the controller 124 for capacitive sensing of debris 102 disposed at least partially within the acoustic port 126 such that the debris at least partially occludes the acoustic port. In one or more embodiments, the controller 124 can, therefore, be adapted to detect a change in capacitance of the capacitor 154. Such change in capacitance can be associated with debris 102 at least partially occluding the acoustic port 126.

Any suitable technique or techniques can be utilized to detect this change in capacitance. For example, the device 100 can measure a reference capacitance between the first electrode 150 and the second electrode 152 prior to use by the user or when the acoustic port is unobstructed. Such reference capacitance represents the capacitance of the capacitor 154 when the acoustic port is unobstructed. The device 100 can further measure a second capacitance between the first electrode 150 and the second electrode 152. A determination can be made as to whether the acoustic port 126 is at least partially occluded if the second capacitance is greater than the reference capacitance. In other words, the debris 102 can increase a dielectric constant of the capacitor 154, thereby increasing the capacitance. In one or more embodiments, the controller 124 can further be adapted to notify the user or a technician that the acoustic port 126 is at least partially occluded if a change of capacitance is detected. Any suitable technique or techniques can be utilized to provide this notification.

The controller 124 and the sensor 138 can be utilized to detect any debris 102 disposed at least partially within the acoustic port 126. In one or more embodiments, the debris 102 can include earwax that can be produced by the user. Such debris 102 can affect the performance of the hearing device 100 by preventing acoustic energy produced by the speaker 120 from being directed through the acoustic port 126 to the user.

The capacitor 154 can include any suitable type of electrodes 150, 152, e.g., at least one ring electrode. The first electrode 150 can be the same as the second electrode 152. In one or more embodiments, the first electrode 150 can include a type of electrode that is different from the electrode utilized for second electrode 152. Further, although depicted as including first and second electrodes 150, 152, the capacitor 154 can include any suitable number of electrodes disposed adjacent to or at least partially within the acoustic port 126. Further, the electrodes 150, 152 can be arranged in any suitable position relative to each other. For example, in the embodiment illustrated in FIG. 2, the electrodes 150, 152 are arranged such that they are separated by a plate separation distance 104 in a direction that is substantially parallel to a port axis 106.

Figure 3:
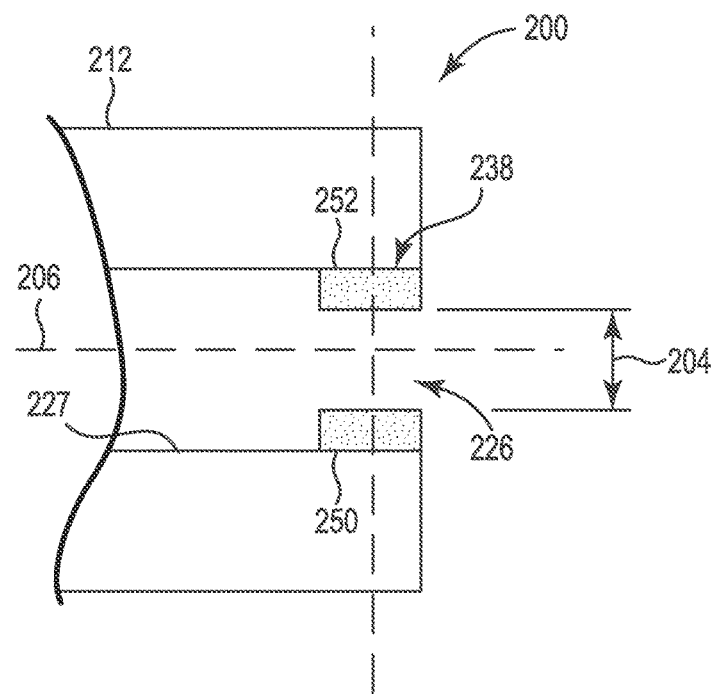
FIG. 3 is a schematic cross-section view of a portion of another embodiment of a hearing device.
Figure 4:
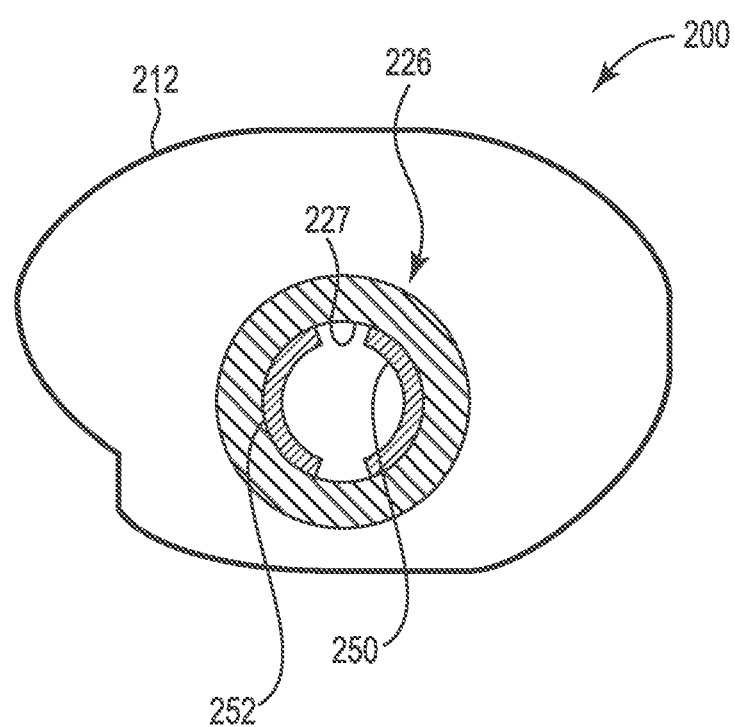
FIG. 4 is a schematic plan view of a portion of the hearing device of FIG. 3.

As mentioned herein, a capacitive sensor of a hearing device can include any suitable type of electrodes and be disposed in any suitable relationship to a port of the hearing device. For example, FIGS. 3-4 are various views of a portion of another embodiment of a hearing device 200 that includes a capacitive sensor 238. All of the design considerations and possibilities described herein regarding the hearing device 10 of FIG. 1 and the hearing device 100 of FIG. 2 apply equally to the hearing device 200 of FIGS. 3-4. Although depicted as being disposed within an acoustic port 226 of the hearing device 200, the sensor 238 can be disposed at least partially within a microphone port (e.g., microphone port 28 of FIG. 1). One difference between hearing device 200 and hearing devices 10 and 100 is that sensor 238 includes a first electrode 250 and a second electrode 252 that are each partial ring electrodes having a plate separation distance 204 as measured in a direction that is substantially orthogonal to a port axis 206 of acoustic port 226. Each of the electrodes 250, 252 can take any suitable shape or shapes and have any suitable dimensions. Further, the electrodes 250, 252 can also be separated by any suitable distance as measured in a direction along an inner surface 227 of the acoustic port 226. The electrodes 250, 252 can be disposed along any suitable portion or portions of the acoustic port 226. In one or more embodiments, at least a portion of the electrodes 250, 252 can extend beyond an opening 228 of the acoustic port.

Although not shown, the electrodes 250, 252 can be electrically connected to a controller (e.g., controller 24 of hearing device 10 of FIG. 1) disposed in a housing 212 of the hearing device 200.

Figure 5:
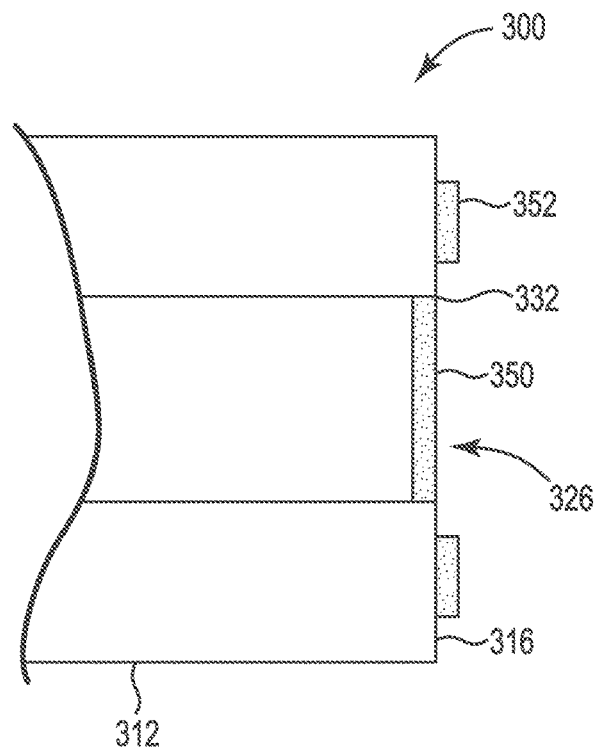
FIG. 5 is a schematic cross-section view of another embodiment of a hearing device.
Figure 6:
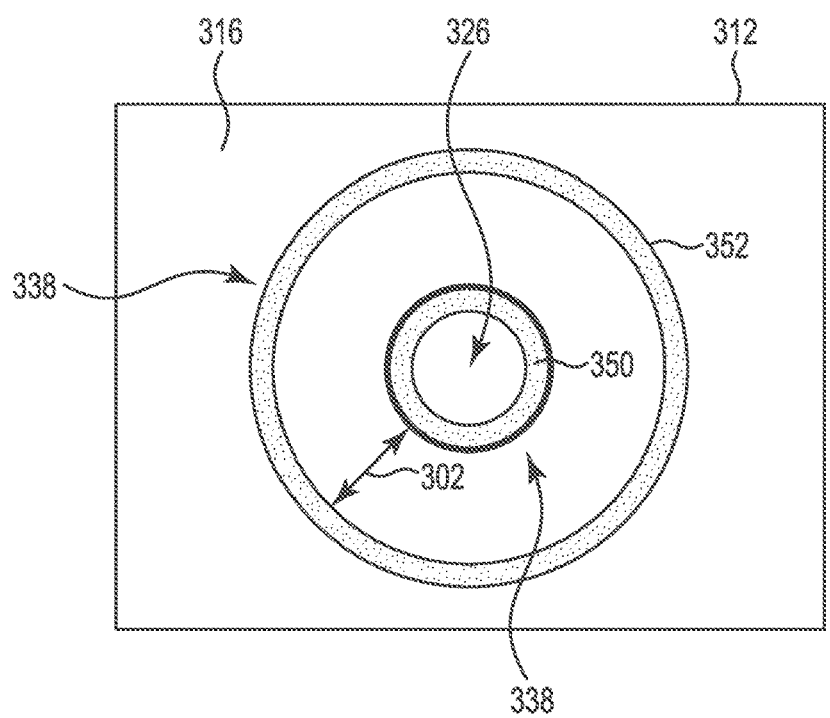
FIG. 6 is a schematic plan view of a portion of the hearing device of FIG. 5.

As mentioned herein, at least a portion of the sensor can be disposed adjacent to a port but not necessarily within the port. For example, FIGS. 5-6 are various views of another embodiment of a hearing device 300. All of the design considerations and possibilities described herein regarding the hearing device 10 of FIG. 1 and hearing device 100 of FIG. 2 apply equally to the hearing device 300 of FIGS. 5-6. One difference between hearing device 300 and hearing devices 10 and 100 is that sensor 338 includes a first electrode 350 disposed at least partially within a first end 332 of acoustic port 326, and a second electrode 352 is disposed on an outer surface 316 of a housing 312 of the hearing device 300. The second electrode 352 is spaced apart from the first electrode 350 along the outer surface 316 of the housing 312 any suitable distance 302. Although not shown, each of the first and second electrodes 350, 352 is electrically connected to a controller disposed within the housing 312 of the hearing device 300. The port 326 can include any suitable port. In one or more embodiments, the port 326 is an acoustic port that is acoustically connected to a speaker or receiver. Further, in one or more embodiments, the port 326 is a microphone port that is acoustically connected to a microphone.

The first and second electrodes 350, 352 can include any suitable type of electrode. In one or more embodiments, each of the first and second electrodes 350, 352 is a ring electrode. As shown in FIGS. 5-6, the second electrode 352 encircles or encloses the first electrode 350 and the first end 332 of the port 326. Any suitable portion or portions of the first electrode 350 can be disposed within the port 326. In one or more embodiments, the first electrode 350 is disposed entirely within the port 326.

The sensor 338 can be adapted to detect debris disposed at least partially on the outer surface 316 of the housing 312 and adjacent to the port 326. In one or more embodiments, the device 300 detects a change of capacitance of the sensor 338 that can indicate that debris is disposed adjacent to or within the port 326. The device 300 can utilize any suitable technique or techniques to detect this change of capacitance. In one or more embodiments, the controller (e.g., controller 24 of FIG. 1) can be adapted to compare a capacitance of the sensor 338 prior to use (i.e., the reference capacitance) or after the device 300 has been cleaned, and a second capacitance of the sensor after the hearing device 300 has been utilized by a user. If the second capacitance is greater than the reference capacitance, then debris may be positioned adjacent to or within the port 326.

Figure 7:
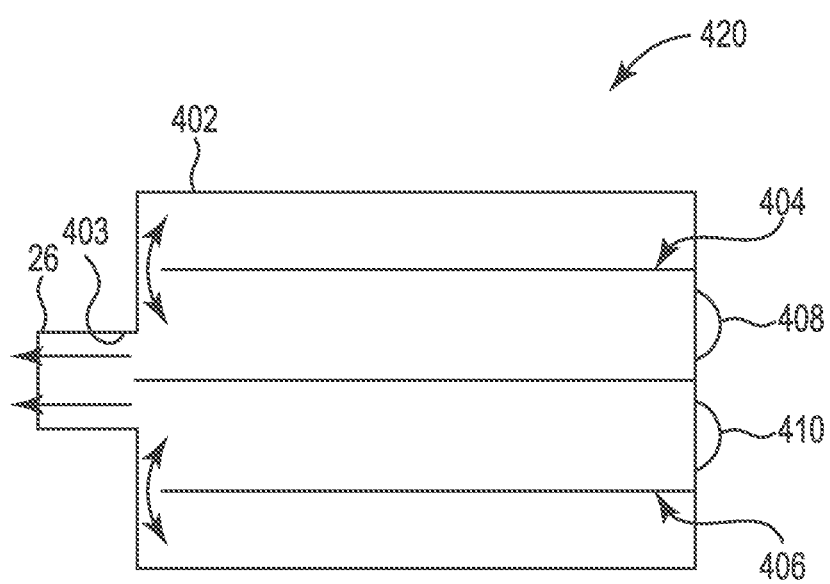
FIG. 7 is a schematic cross-section view of one embodiment of a speaker.

The various embodiments of hearing devices described herein can include any suitable type of sensor or sensors that are adapted to assist the devices in detecting whether one or more ports are at least partially occluded by debris. In one or more embodiments, at least one of the speaker or microphone of the device can be utilized as a sensor to detect at least partial occlusion of a port. For example, FIG. 7 is a schematic cross-section view of an embodiment of a speaker 420 that can be utilized with any suitable hearing device, e.g., hearing device 10 of FIG. 1. Although described in reference to hearing device 10 of FIG. 1, the speaker 420 can be utilized with any suitable hearing device. Further, all of the design considerations and possibilities described herein regarding the speaker 20 of the hearing device 10 of FIG. 1 apply equally to the speaker 420 of FIG. 7.

The speaker 420 includes a housing 402 and an opening 403 disposed in the housing that is acoustically connected to an acoustic port 426 of a hearing device (e.g., acoustic port 26 of hearing device 10 of FIG. 1). The speaker 420 can include any suitable speaker. As illustrated in FIG. 7, the speaker 420 is a dual motor assembly speaker that includes a first diaphragm 404 connected to a first motor 408 and a second diaphragm 406 electrically connected to a second motor 410. The first and second diaphragms 404, 406 can be disposed in any suitable relationship relative to each other. In one or more embodiments, the first diaphragm 404 is substantially parallel to the second diaphragm 406.

In one or more embodiments, speaker 420 is electrically connected to the controller 24 of hearing device 10. The controller 24 can be adapted to direct an acoustic signal to the first diaphragm 404 such that the first diaphragm converts the acoustic signal to a reference sound wave that is transmitted into an ear canal through the acoustic port 26 when the port is not at least partially occluded. The reference sound wave can include any suitable waveform. The controller 24 can also be adapted to detect a second sound wave utilizing the second diaphragm 406. The second sound wave can include at least a portion of the reference sound wave that has been reflected by the ear canal or eardrum within the ear canal and directed into the acoustic port 26. In other words, the second diaphragm 406 of speaker 420 can be utilized as a sensor that detects acoustic energy that is directed into the ear canal and reflected back through the acoustic port 26.

The controller 24 can further be adapted to compare a sound pressure level of the reference sound wave to a sound pressure level of the second sound wave, and determine whether the acoustic port 26 is at least partially occluded based upon the comparison of the sound pressure level of the reference sound wave to the sound pressure level of the second sound wave. In one or more embodiments, the acoustic port 26 can be at least partially occluded by debris if the sound pressure level of the second sound wave is less than a sound pressure level of the reference sound wave. The controller 24 can also be adapted to notify a user or technician that the acoustic port 26 is at least partially occluded based upon the comparison of the sound pressure level of the reference sound wave to the sound pressure level of the second sound wave.

Figure 8:
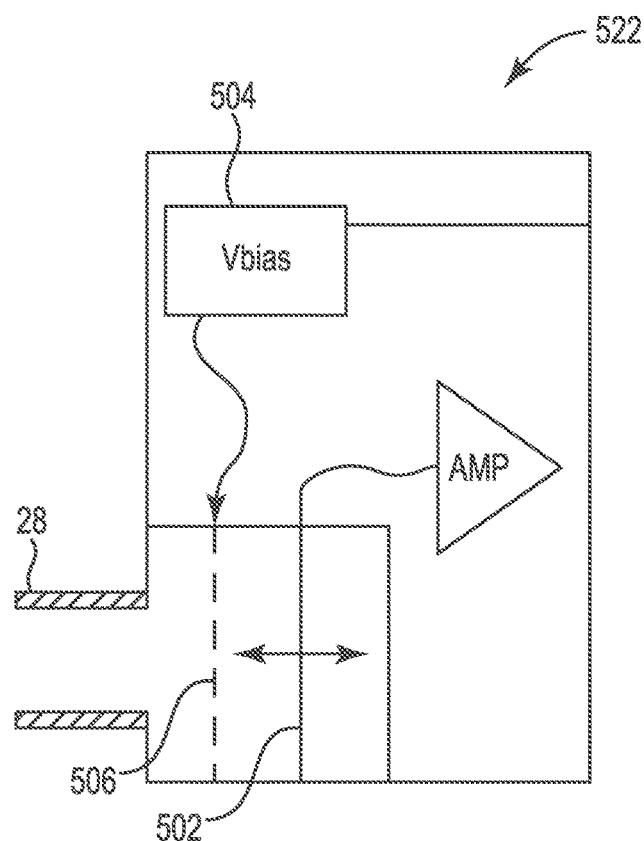
FIG. 8 is a schematic cross-section view of one embodiment of a microphone.

As mentioned herein, a microphone of a hearing device can also be adapted to be utilized as a sensor for detecting occlusion of a port. For example, FIG. 8 is a schematic plan view of one embodiment of a microphone 522. All of the design considerations and possibilities described herein regarding the microphone 22 of hearing device 10 of FIG. 1 apply equally to the microphone 522 of FIG. 8. The microphone 522 is acoustically connected to the microphone port 28 of hearing device 10 using any suitable technique or techniques. The microphone 522 also includes a diaphragm 502.

The microphone 522 can include any suitable microphone. In one or more embodiments, the microphone 522 includes a micro electromechanical (MEMS) microphone. In general, MEMS microphones have an internal diaphragm bias source, unlike electret microphones in which the diaphragm bias voltage is embedded within the diaphragm. By controlling the MEMS microphone bias voltage the MEMS microphone diaphragm can be excited into mechanical vibration. If an electrical bias voltage pulse is sent to the diaphragm, the diaphragm will "ring" (resonate at a rate that is determined by the mechanical and acoustical properties of the microphone). The mechanical structure of the microphone does not change, so acoustic changes to the microphone can be detected. The largest acoustic change that can occur to the microphone can be caused by an occlusion of the microphone port.

An electrical impulse signal applied to the diaphragm will induce mechanical motion to the diaphragm, thereby resulting in a damped wave response. With the microphone port open, the diaphragm will decay at a specific rate. If the microphone port becomes at least partially occluded, an acoustic compliance is created that will result in a differing decay rate of the diaphragm. This signal can be detected and measured by the controller of the hearing device.

In operation, the speaker outputs a low-level tone that the microphone would detect if there are no obstructions. If a port blockage is detected, the microphone or speaker could be blocked. To determine which is blocked, the microphone would run through a routine that electrically stimulates the diaphragm into vibration and measures the response. If the response does not fall within a predefined range of expected values, the microphone port is blocked. If the speaker is blocked, then the microphone routine would fall within a predefined range matching the reference value, indicating that the microphone is not blocked.

Figure 9:
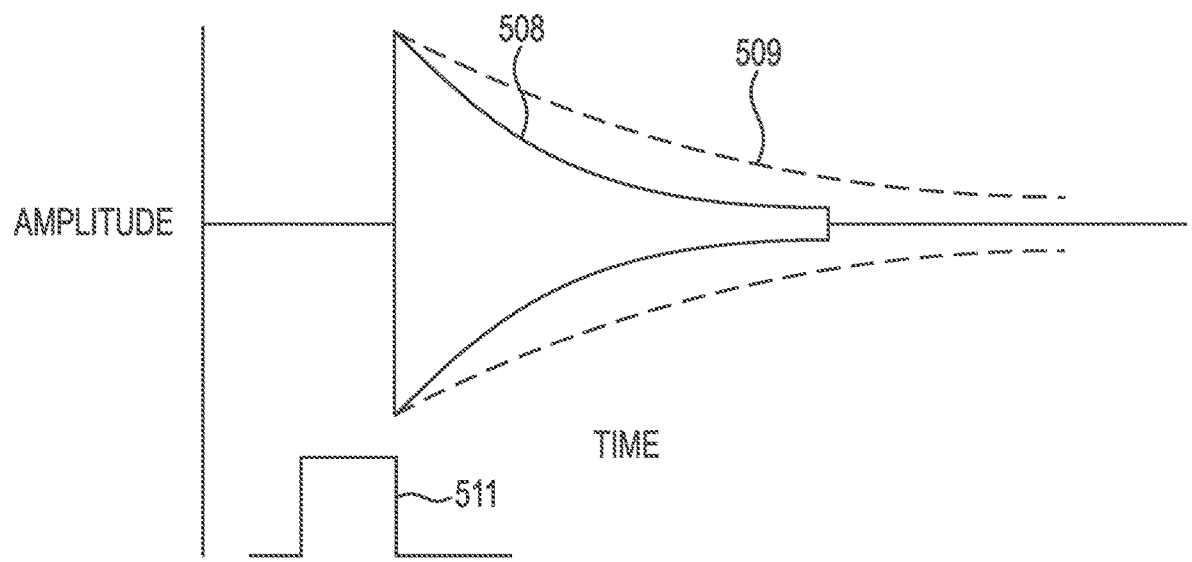
FIG. 9 is a graph of amplitude versus time of exemplary mechanical resonance curves for the microphone of FIG. 8.

The controller 24 of hearing device 10 can be adapted to direct a first electrical pulse to the microphone diaphragm 502 and determine a reference decay rate of a mechanical resonance signal of the microphone diaphragm in response to the first electrical pulse when the microphone port 26 is unobstructed. Any suitable technique or techniques can be utilized to determine the decay rate of the mechanical resonance signal of the microphone diaphragm 502. Further, any suitable electrical pulse can be utilized for the first electrical pulse. For example, FIG. 9 is a graph of amplitude versus time of microphone 522 in response to a first electrical pulse 511. As shown in FIG. 7, the first electrical pulse 511 includes a square wave that can be applied by a voltage source 504 of the microphone 522 via bias grid 506 as shown in FIG. 8. The decay rate of the mechanical resonance signal of the diaphragm 502 of the microphone 522 in response to the first electrical pulse 511 can be determined when the microphone port 28 is free of debris. As can be seen in FIG. 9, the microphone 522 exhibits a mechanical resonance signal 508 that has a measured reference decay rate when the microphone port 28 is unobstructed.

The controller 24 can further be adapted to direct a second electrical pulse to the microphone diaphragm 502 using the bias voltage source 504 and the bias grid 506. The second electrical pulse can include any suitable wave form. In one or more embodiments, the second electrical pulse includes a bias voltage pulse. The controller 24 can further be adapted to determine a second decay rate of a second mechanical resonance signal of the microphone diaphragm 502 in response to the second electrical pulse using any suitable technique or techniques. As shown in FIG. 9, the diaphragm 502 exhibits a second mechanical resonance signal 509 that has a second decay rate that is different from a reference decay rate of the first mechanical resonance signal 508. The controller 24 can be adapted to compare the reference decay rate of the first mechanical resonance signal 508 to the second decay rate of the second mechanical resonance signal 509 and determine whether the microphone port 28 is at least partially occluded by debris if the second decay rate is greater than the reference decay rate, which is shown in FIG. 9. In one or more embodiments, the controller 24 can be further adapted to notify a user or technician that the microphone port 28 is at least partially occluded if the second decay rate is within a predefined range or greater than the reference decay rate.

Figure 10:
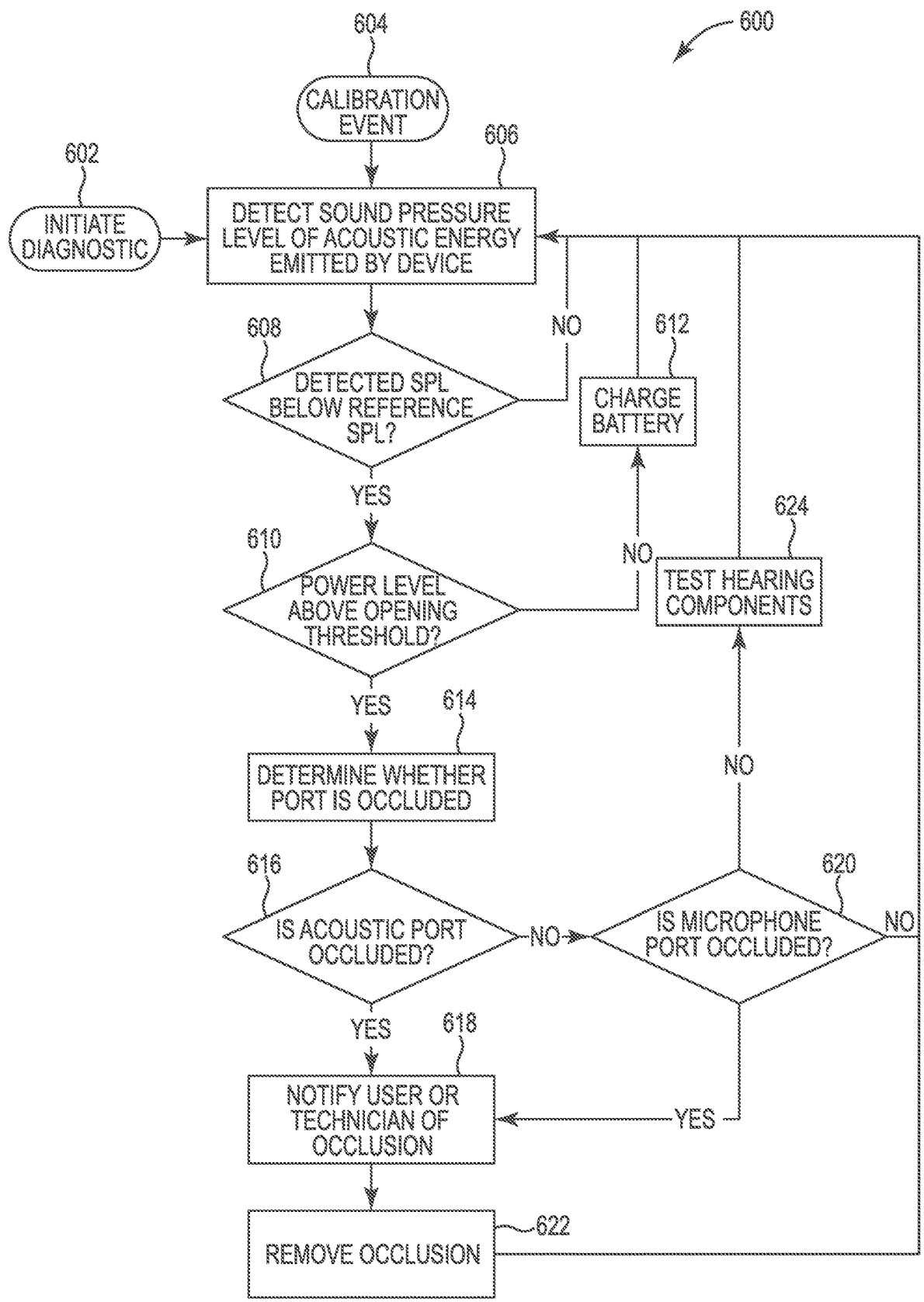
FIG. 10 is a flowchart of one embodiment of a method that can be utilized with a hearing device.

Any suitable technique or techniques can be utilized with the various embodiments of hearing devices described herein to determine whether a port of the hearing device is at least partially occluded. For example, FIG. 10 is a flowchart of one embodiment of a method 600 that can be utilized with the hearing device 10 of FIG. 1. Although described in reference to hearing device 10, the method 600 can be used with any suitable hearing device. At 602, the user or the controller 24 can initiate a diagnostic routine (i.e., method 600) using any suitable technique or techniques. Such diagnostic routine can be initiated by the user through any suitable application on a smartphone or other device that is connected to the hearing device. Further, the user or the controller 24 can initiate a calibration event at 604 using any suitable technique or techniques. The calibration event can detect a sound pressure level of acoustic energy emitted by the device at 606 and compare such sound pressure level to a reference sound pressure level that is stored in memory of the device 10 during testing of the device when the ports 26, 28 are unobstructed. Any suitable technique or techniques can be utilized to detect the sound pressure level of acoustic energy emitted by the device. For example, the controller 24 can send an electrical signal to the speaker 20, which converts the signal to acoustical energy that is directed by the speaker through the speaker port 26. At least a portion of the acoustical energy directed through the acoustic port 26 can be directed into the microphone port 28 and detected by the microphone 22. The hearing device 10 can compare the detected sound pressure level to a reference sound pressure level of acoustic energy emitted by the hearing device when neither of the ports 26, 28 is occluded. Such reference sound pressure level can be determined during testing of the device prior to use by the user. If the detected sound pressure level is equal to or greater than a reference sound pressure level, then the device can continue to detect a sound pressure level of acoustic energy emitted by the device at 606 or the method 600 can be terminated.

If, however, the detected sound pressure level is less than the reference sound pressure level at 608, then the hearing device 10 compares a power level of the power source 42 of the hearing device to an operating threshold of the device at 610. If the power level is below such operating threshold, then the device 10 notifies the user or a technician that the power source 42 needs to be charged at 612. If the power level of the power source 42 is above the operating threshold, then the device 10 determines whether at least one of the acoustic port 26 or the microphone port 28 is at least partially occluded by debris at 614. Any suitable technique or techniques can be utilized to determine whether at least one of the ports 26, 28 is at least partially occluded.

Figure 11:
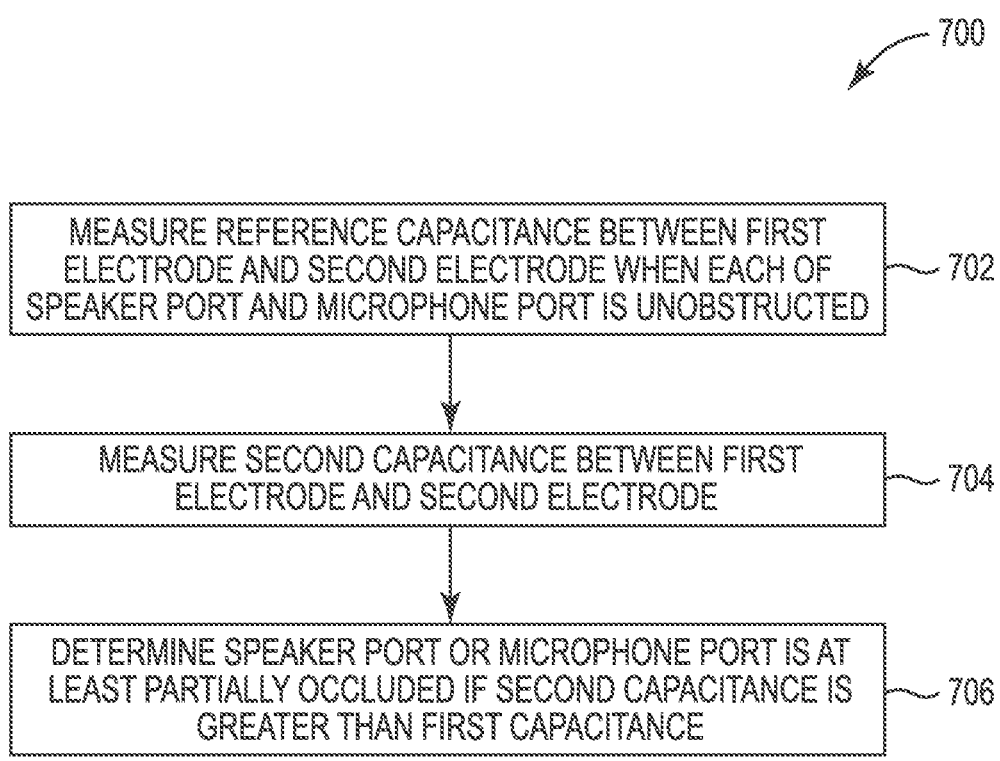
FIG. 11 is a flowchart of one embodiment of a method of determining whether a port is at least partially occluded.

FIG. 11 is a flowchart of one embodiment of a method 700 that can be utilized to determine whether a port of the hearing device 10 is at least partially occluded. Although described regarding the hearing device 10 of FIG. 1, the method 700 can be utilized with any suitable hearing device. At 702, the device 10 can utilize one or both sensors 38, 40 to measure a reference capacitance between a first electrode disposed at least partially within the acoustic port or the microphone port and a second electrode disposed on a housing of the hearing device when each of the acoustic port and microphone port is unobstructed. For example, as described herein regarding sensor 338 of hearing device 300 of FIGS. 5-6, the device measures a reference capacitance between the first electrode 350 disposed at least partially within the acoustic port 326 and the second electrode 352 disposed on the outer surface 316 of the housing 312 of the hearing device when the acoustic port is unobstructed. Similarly, sensor 40 disposed adjacent to microphone port 28 of device 10 can utilize first and second electrodes disposed in a similar configuration as first and second electrodes 350, 352 to determine a reference capacitance. At 704, the device measures a second capacitance between the first electrode 350 and the second electrode 352 using any suitable technique or techniques. At 706, the device 10 determines that either the acoustic port 26 or the microphone port 28 is at least partially occluded if the second capacitance is greater than the reference capacitance.

Returning to FIG. 10, the device 10 determines whether the acoustic port 26 is at least partially occluded at 616 using any suitable technique or techniques. Further, for example, the device 10 can determine whether the microphone port 28 is at least partially occluded at 620 using any suitable technique or techniques. Although shown and described as determining whether the acoustic port 26 is at least partially occluded prior to determining whether the microphone port 28 is at least partially occluded, method 600 can first determine whether the microphone port is at least partially occluded, or the method can simultaneously determine whether at least one of the acoustic port or the microphone port is at least partially occluded.

Figure 12:
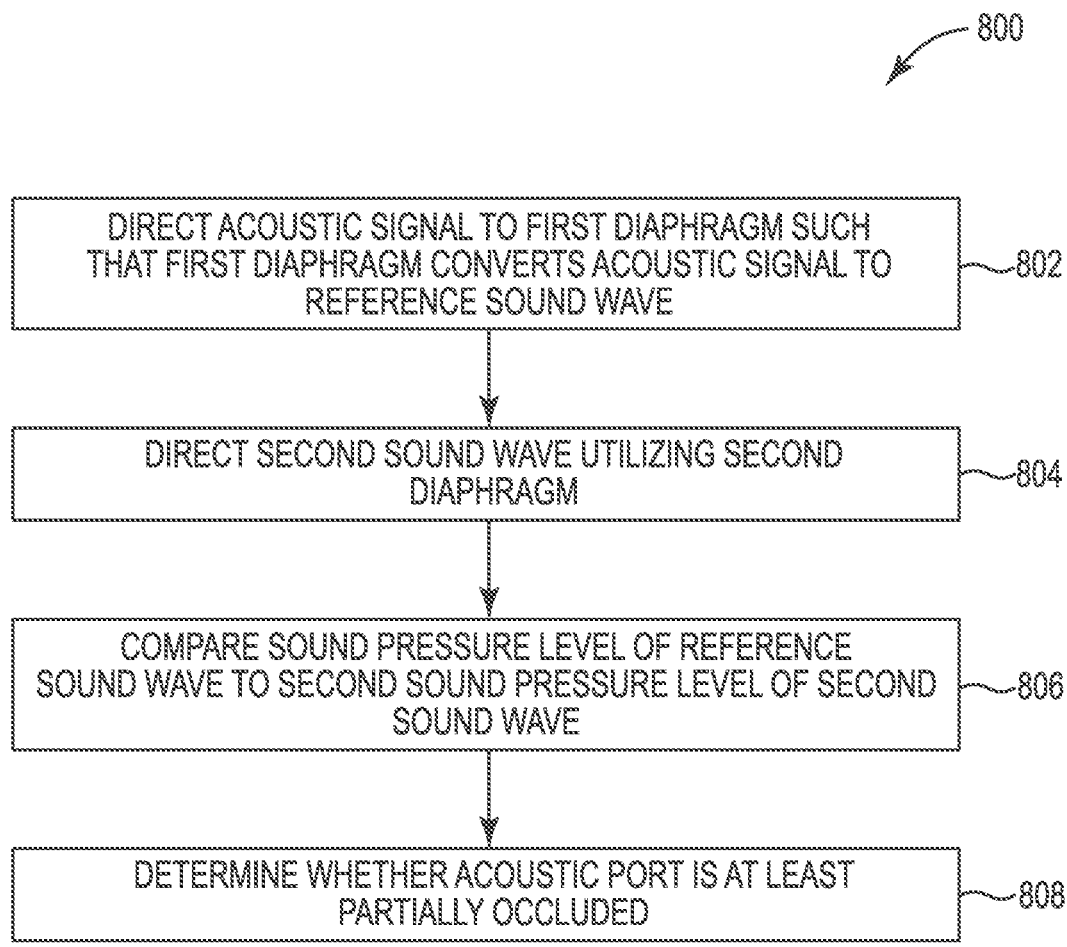
FIG. 12 is a flowchart of one embodiment of a method of determining whether a speaker port is at least partially occluded.

To determine whether the acoustic port is at least partially occluded at 616, the device can utilize method 800 of FIG. 12. The method 800 can be utilized with any suitable hearing device, e.g., hearing device 10 of FIG. 1. Further, such hearing device can include any suitable speaker. For example, speaker 420 of FIG. 9 can be utilized with method 800 to determine whether the acoustic port 26 is at least partially occluded. At 802, the device 10 directs an acoustic signal to the first diaphragm 404 of speaker 420 such that the first diaphragm converts the acoustic signal to a reference sound wave. Such reference sound wave is measured prior to occlusion of the acoustic port 26, e.g., during initial fitting of the hearing device. In one or more embodiments, a reference sound wave can be measured when the hearing device 10 is disposed within a housing of a charging base or device. As a result, two or more reference sound waves can be measured in different settings and utilized as a baseline for measuring subsequent sound waves to determine occlusion of the acoustic port. The reference sound wave can be any suitable waveform. At 804, the device 10 detects a second sound wave utilizing the second diaphragm 406 of speaker 420 using any suitable technique or techniques. The second sound wave can be a portion of the reference sound wave that is reflected by the ear canal or eardrum of the user and directed back through the acoustic port 26 to the speaker 20. In one or more embodiments, the second sound wave can be measured when the hearing device 10 is disposed within a housing of a charging base or device. The sound pressure level of the reference sound wave can be compared to the sound pressure level of the second sound wave at 806 using any suitable technique or techniques. For example, the controller 24 of device 10 can compare the sound pressure levels of the reference sound wave and the second sound wave using any suitable techniques. At 808, the device 10 determines whether the acoustic port 26 is at least partially occluded if the sound pressure level of the second sound wave is greater than the sound pressure level of the reference sound wave using any suitable technique or techniques.

Returning to FIG. 10, if the acoustic port 26 is at least partially occluded at 616, then the method 600 notifies the user or technician at 618 of the occlusion. Such notification can be made using any suitable technique or techniques. For example, a smartphone connected to the hearing device 10 can display a message to the user that the acoustic port 26 is at least partially occluded utilizing a software interface for the device that is stored in memory of the smartphone or accessed through the cloud by the smartphone. If, however, the device 10 determines that the acoustic port 26 is not at least partially occluded, then the method 600 determines whether the microphone port 28 is at least partially occluded using any suitable technique or techniques at 620.

Figure 13:
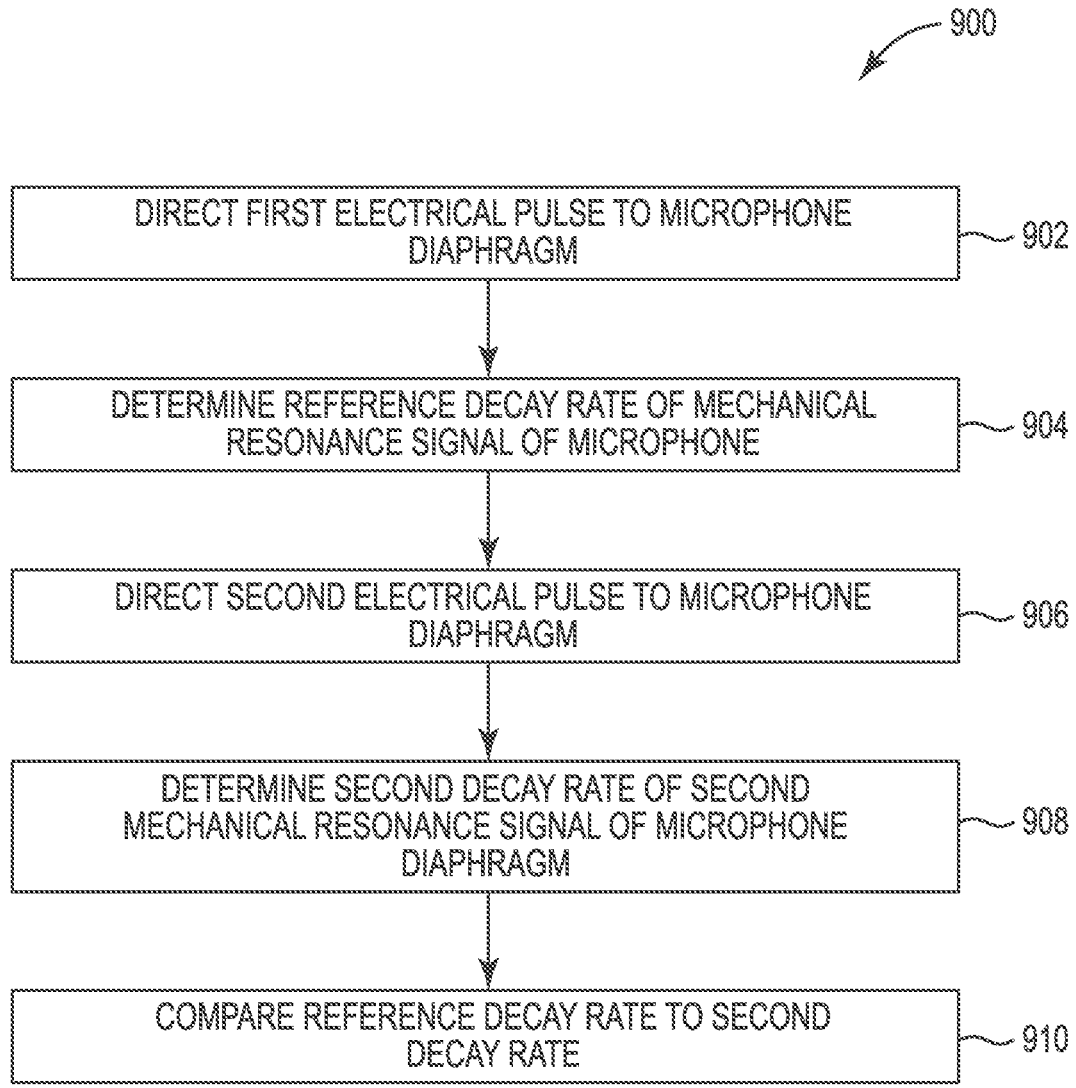
FIG. 13 is a flowchart of one embodiment of a method of determining whether a microphone port is at least partially occluded.

FIG. 13 is a flowchart of one embodiment of a method 900 for determining whether the microphone port 26 is at least partially occluded at 620 of method 600 of FIG. 10. The method 900 can be utilized with any suitable hearing device, e.g., hearing device 10 of FIG. 1. Further, the method 900 can be utilized with any suitable microphone, e.g., microphone 522 of FIGS. 8-9. At 902, the device 10 directs a first electrical pulse to the microphone diaphragm 502 using any suitable technique or techniques. At 904, the device 10 determines a reference decay rate of a mechanical resonance signal of the microphone 522. In one or more embodiments, determination of the decay rate of a mechanical resonance signal of the microphone 22 can be determined prior to use by the user such that the decay rate is a baseline that can be stored in memory and utilized in method 900. As shown in FIG. 9, bias voltage pulse is sent to the microphone diaphragm 502, which in turn results in decay rate of the mechanical resonance signal 508 of the microphone. The device 10 further directs a second electrical pulse to the microphone diaphragm 502 at 906 using any suitable technique or techniques. At 908, the device determines a second decay rate of a second mechanical resonance signal 509 of the microphone diaphragm 502 using any suitable technique or techniques. At 910, the device 10 compares the second decay rate to the reference decay rate. If the second decay rate is greater than the reference decay rate, then the method 600 of FIG. 12 notifies the user or technician at 618 of method 600 that the microphone port 28 is at least partially occluded. Any suitable technique or techniques can be utilized to compare the second decay rate to the reference decay rate. If, however, the second decay rate is less than or equal to the reference decay rate, then the method 600 returns to detecting sound pressure level of the acoustic energy device at 606 or terminates the method.

In one or more embodiments, the method 600 of FIG. 10 can also include removing the debris or occlusion from at least one of the acoustic port 26 or the microphone port 28 at 622 using any suitable technique or techniques. A wax filter or trap may be disposed over at least one of the acoustic port 26 or the microphone port 28. Such wax filter can be cleaned using any suitable technique or techniques, e.g., by the application of heat, mechanical energy such as vibrational energy, carbamide peroxide, etc. These cleaning techniques can be applied by the user while the hearing device 10 is out of a charging case or when the hearing device is placed within the charging case. Such techniques can be applied manually or automatically using any suitable techniques.

If the method 600 determines that the microphone port 28 is not occluded at 620, then either one or more of the hearing components 18 can be tested at 624 to determine whether such component or components are not functioning as required, or the method can return to the initiation of the diagnostic by detecting sound pressure level of acoustic energy emitted by the device 10 at 606. Any suitable technique can be utilized to test one or more of the hearing components at 624. Although not shown, if the method 600 determines that the microphone port is not occluded at 620, then the method can be terminated.

Although the method 600 is illustrated as including particular operations performed in a particular order, it is understood that this is in an exemplary method. In various embodiments, various orders of the same, similar, or different operations may be performed without departing from the scope of the present disclosure.

All references and publications cited herein are expressly incorporated herein by reference in their entirety into this disclosure, except to the extent they may directly contradict this disclosure. Illustrative embodiments of this disclosure are discussed, and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed is:

1. A hearing device comprising:
  a housing comprising an inner surface and an outer surface;
  electronic components disposed within the housing and comprising a speaker, a microphone, and a controller electrically connected to the speaker and the microphone;
  a port disposed in the housing extending between a first end at the outer surface of the housing and a second end disposed within the housing, wherein the port is acoustically connected to at least one of the speaker or the microphone; and
  a sensor comprising a first electrode and a second electrode each electrically connected to the controller, wherein the first electrode is disposed at least partially within the first end of the port, and further wherein the second electrode is disposed on the outer surface of the housing and spaced apart from the first electrode;
  wherein the controller is adapted to detect a change in capacitance of the sensor, wherein the change in capacitance is associated with debris at least partially occluding the port.

2. The hearing device of claim 1, wherein the port comprises an acoustic port, wherein the speaker is acoustically connected to the acoustic port.

3. The hearing device of claim 1, wherein the port comprises a microphone port, wherein the microphone is acoustically connected to the microphone port.

4. The hearing device of claim 1, wherein at least one of the first electrode or the second electrode comprises a ring electrode.

5. The hearing device of claim 1, wherein the second electrode encircles the first electrode and the first end of the port.

6. The hearing device of claim 1, wherein the first electrode is disposed entirely within the port.

7. The hearing device of claim 1, wherein the controller is further adapted to notify a user or technician that the port is at least partially occluded if a change of capacitance is detected.

8. A hearing device comprising:
  a housing comprising a microphone port disposed through the housing;
  hearing components disposed within the housing and comprising a microphone and a controller electrically connected to the microphone, wherein the microphone is acoustically connected to the microphone port and comprises a diaphragm;
  wherein the controller is adapted to:
    direct a first electrical pulse to the microphone diaphragm;
    determine a reference decay rate of a mechanical resonance signal of the microphone diaphragm in response to the first electrical pulse when the microphone port is unobstructed;
    direct a second electrical pulse to the microphone diaphragm;
    determine a second decay rate of a second mechanical resonance signal of the microphone diaphragm in response to the second electrical pulse;
    compare the reference decay rate to the second decay rate; and
    determine whether the microphone port is at least partially occluded by debris if the second decay rate is greater than the reference decay rate.

9. The hearing device of claim 8, wherein the microphone comprises a microelectromechanical microphone.

10. The hearing device of claim 8, wherein the controller is further adapted to notify a user or technician that the microphone port is at least partially occluded if the second decay rate is greater than the reference decay rate.

11. The hearing device of claim 8, wherein the hearing components further comprise a speaker acoustically connected to an acoustic port that is disposed through the housing.

12. The hearing device of claim 11, wherein the controller is further adapted to:
  direct an acoustic signal to the speaker such that the speaker converts the acoustic signal to a reference sound wave that is transmitted into an ear canal through the acoustic port;
  detect a second sound wave utilizing the second diaphragm, wherein the second sound wave comprises at least a portion of the reference sound wave that is reflected by an eardrum within the ear canal and directed into the acoustic port;

compare a sound pressure level of the reference sound wave to a sound pressure level of the second sound wave; and determine whether the acoustic port is at least partially occluded based upon the comparison of the sound pressure level of the reference sound wave to the sound pressure level of the second sound wave.

13. The hearing device of claim 12, wherein the controller is further adapted to notify a user or technician that the acoustic port is at least partially occluded based upon the comparison of the sound pressure level of the reference sound wave to the sound pressure level of the second sound wave.

14. The hearing device of claim 8, wherein the second electrical pulse comprises a bias voltage pulse.

15. A method comprising:

detecting a sound pressure level of acoustic energy emitted by a hearing device;

comparing the detected sound pressure level to a reference sound pressure level of acoustic energy emitted by the hearing device;

if the detected sound pressure level is less than the reference sound pressure level, then comparing a power level of a power source of the hearing device to an operating threshold;

if the power level is above the operating threshold, then determining whether at least one of an acoustic port or a microphone port is at least partially occluded by debris; and notifying a user or a technician if at least one of the acoustic port or the microphone port is at least partially occluded.

16. The method of claim 15, further comprising removing the debris from at least one of the acoustic port or microphone port.

17. The method of claim 15, wherein determining whether at least one of the acoustic port or microphone port is at least partially occluded by debris comprises:

measuring a reference capacitance between a first electrode disposed at least partially within the acoustic port or the microphone port and a second electrode disposed on a housing of the hearing device when each of the acoustic port and microphone port is unobstructed;

measuring a second capacitance between the first electrode and the second electrode; and determining that the acoustic port or microphone port is at least partially occluded if the second capacitance is greater than the reference capacitance.

18. The method of claim 15, wherein determining whether at least one of the acoustic port or microphone port is at least partially occluded by debris comprises:

directing a first electrical pulse to a diaphragm of a microphone disposed in a housing of the hearing device, wherein the microphone is acoustically connected to the microphone port;

determining a reference decay rate of a mechanical resonance signal of the microphone diaphragm in response to the first electrical pulse when the microphone port is unobstructed;

directing a second electrical pulse to the microphone diaphragm;

determining a second decay rate of a second mechanical resonance signal of the microphone diaphragm in response to the second electrical pulse;

comparing the reference decay rate to the second decay rate; and determining that the microphone port is at least partially occluded by debris if the second decay rate is greater than the reference decay rate.

19. The method of claim 18, further comprising determining that the acoustic port is at least partially occluded by debris if the second decay rate is substantially equal to the reference decay rate.

20. The method of claim 15, wherein determining whether at least one of the acoustic port or microphone port is at least partially occluded by debris comprises:

directing an acoustic signal to a first diaphragm of a speaker disposed within a housing of the hearing device and acoustically connected to the acoustic port such that the first diaphragm converts the acoustic signal to a reference sound wave that is transmitted into an ear canal through the acoustic port;

detecting a second sound wave utilizing a second diaphragm of the speaker, wherein the second sound wave comprises at least a portion of the reference sound wave that is reflected by an eardrum within the ear canal and directed into the acoustic port;

comparing a sound pressure level of the reference sound wave to a sound pressure level of the second sound wave; and determining whether the acoustic port is at least partially occluded based upon the comparison of the sound pressure level of the reference sound wave to the sound pressure level of the second sound wave.

* * * * *